United States Patent
Kantrowitz et al.

(10) Patent No.: US 9,273,021 B2
(45) Date of Patent: Mar. 1, 2016

(54) DIBENZOFURAN DERIVATIVES AS INHIBITORS OF FRUCTOSE 1,6-BISPHOSPHATASE AND METHODS OF USE THEREOF

(75) Inventors: Evan R. Kantrowitz, Waban, MA (US); Sabrina Heng, Adelaide (AU)

(73) Assignee: TRUSTEES OF BOSTON COLLEGE, Chestnut Hill, MA (US)

( * ) Notice: Subject to any disclaimer, the term of this patent is extended or adjusted under 35 U.S.C. 154(b) by 872 days.

(21) Appl. No.: 13/147,964

(22) PCT Filed: Feb. 4, 2010

(86) PCT No.: PCT/US2010/023207
§ 371 (c)(1),
(2), (4) Date: Oct. 19, 2011

(87) PCT Pub. No.: WO2010/091185
PCT Pub. Date: Aug. 12, 2010

(65) Prior Publication Data
US 2012/0028892 A1    Feb. 2, 2012

Related U.S. Application Data

(60) Provisional application No. 61/150,066, filed on Feb. 5, 2009.

(51) Int. Cl.
*C07D 307/91* (2006.01)
*A61P 3/10* (2006.01)

(52) U.S. Cl.
CPC .................. *C07D 307/91* (2013.01)

(58) Field of Classification Search
None
See application file for complete search history.

(56) References Cited

U.S. PATENT DOCUMENTS

2003/0055103 A1    3/2003    Heinzen et al.

FOREIGN PATENT DOCUMENTS

| WO | 2006129318 A2 | 12/2006 |
|---|---|---|
| WO | 2008057254 A2 | 5/2008 |

(Continued)

OTHER PUBLICATIONS

Ettmayer, P., et al. J. Med. Chem. (2004), 47(10); pp. 2393-2404.*

(Continued)

*Primary Examiner* — Kevin S Orwig
(74) *Attorney, Agent, or Firm* — Nixon Peabody LLP

(57) ABSTRACT

The invention is directed to a compound according to formula (I). The compounds of formula (I) include prodrugs, pharmaceutically acceptable salts, stereoisomer mixtures, and enantiomers thereof. The invention is also directed to a pharmaceutical composition comprising a compound according to formula (I) and a pharmaceutically acceptable carrier and to methods for treating diabetes by administering such a pharmaceutical composition alone or in combination with other therapeutic agents. The invention is also directed to inhibitors of fructose-1,6-bisphosphatase.

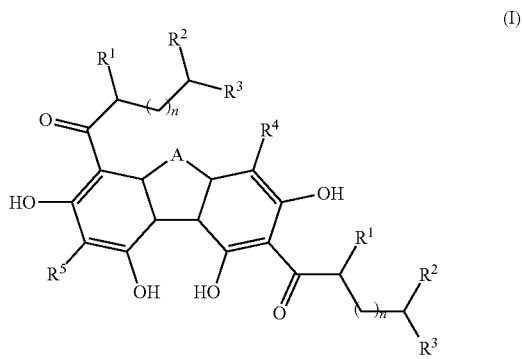

16 Claims, 2 Drawing Sheets

(56) References Cited

FOREIGN PATENT DOCUMENTS

WO 2008119017 A1 10/2008
WO 2008137816 A2 11/2008

OTHER PUBLICATIONS

Heng, S. Ph.D. thesis, Boston College; available at least by May 2009.*

Carney, J.R., "Achyrofuran, a New Antihyperglycemic Dibenzofuran from the South American Medicinal Plant Achyrocline satureioides," J. Nat. Prod., 2002, 65, pp. 203-205.

International Search Report from International Application No. PCT/US2010/023207.

Wright, S. W.; Carlo, A. A.; Carty, M. D.; Danley, D. E.; Hageman, D. L.; Karam, G. A.; Levy, C. B.; Mansour, M. N.; Mathiowetz, A. M.; McClure, L. D.; Nestor, N. B.; McPherson, R. K.; Pandit, J.; Pustilnik, L. R.; Schulte, G. K.; Soeller, W. C.; Treadway, J. L.; Wang, I. K.; Bauer, P. H. "Anilinoquinazoline inhibitors of fructose 1,6-bisphosphatase bind at a novel allosteric site: synthesis, in vitro characterization, and X-ray crystallography". J. Med. Chem. 2002, 45, 3865-3877.

Erion, M. D.; van Poelje, P. D.; Dang, Q.; Kasibhatla, S. R.; Potter, S. C.; Reddy, M. R.; Reddy, K. R.; Jiang, T.; Lipscomb, W. N. "MB06322 (CS-917): A potent and selective inhibitor of fructose 1,6-bisphosphatase for controlling gluconeogenesis in type 2 diabetes". Proc. Natl. Acad. Sci. U S A 2005, 102, 7970-7975.

von Geldern, T. W.; Lai, C.; Gum, R. J.; Daly, M.; Sun, C.; Fry, E. H.; Abad-Zapatero, C. "Benzoxazole benzenesulfonamides are novel allosteric inhibitors of fructose-1,6-bisphosphatase with a distinct binding mode". Bioorg. Med. Chem. Lett. 2006, 16, 1811-1815.

Ahmad, S.; Razaq, S. "New synthesis of biflavones of cupressuflavone series". Tetrahedron 1976, 32, 501-506.

Anderson, N. H.; Ollis, W. D.; Underwood, J. G.; Scrowston, R. M. "Constitution of the Dibenzofuran, Psi-Rhodomyrtoxin, isolated from Rhodomyrtus macrocarpa Benth". J. Chem. Soc. (C) 1969, 2403-2408.

Igboechi, C. A.; Parfitt, R. T.; Rowa,n. M. G. "Two Dibenzofuran Derivatives From Fruits of Rhodomyrtus Macrocarpa". Phytochemistry, vol. 23, No. 5, 1984, 1139-1141.

Sargent, M. V.; Stransky, P. O. "Naturally Occurring Dibenzofurans. Part 3. On the Structures of the Rhodomyrtoxins". J. Chem. Soc. Perkin Trans. 1, 1983, 231-239.

Carney, J. R.; Kreninsky, J. M.; Williamson, R. T.; Luo J. "Achyrofuran, a New Antihyperglycemic Dibenzofuran from the South American Medicinal Plant Achyrocline satureioides". J. Nat. Prod. 2002, 65, 203-205.

* cited by examiner

Achyrofuran (1)

(+)-usnic acid (2)

DIBENZOFURAN DERIVATIVES AS INHIBITORS OF FRUCTOSE 1,6-BISPHOSPHATASE AND METHODS OF USE THEREOF

CROSS REFERENCE TO RELATED APPLICATIONS

This application is a 35 U.S.C. §371 National Stage Entry Application of International Application No. PCT/US2010/023207, filed Feb. 4, 2010, which designates the U.S., and which claims benefit under 35 U.S.C. §119(e) of the U.S. Provisional Application No. 61/150,066, filed Feb. 5, 2009, the content of which is incorporated herein by reference in its entirety.

GOVERNMENT SUPPORT

The subject matter of this application was made with support from the National Institutes of Health, NIH Contract/Grant No. 5 R01 GM026237. The U.S. Government has certain rights in this invention.

FIELD OF THE INVENTION

This invention relates to inhibitors of fructose-1,6-bisphosphatase (FBPase), and methods of their use as novel therapeutics for the treatment of type-2 diabetes.

BACKGROUND OF THE INVENTION

Diabetes mellitus (or diabetes) is one of the most prevalent diseases in the world today. Diabetes patients have been divided into two classes, namely type I or insulin-dependent diabetes mellitus and type II or non-insulin dependent diabetes mellitus (NIDDM). NIDDM accounts for approximately 90% of all diabetics and is estimated to affect 12-14 million adults in the U.S. alone (6.6% of the population). NIDDM is characterized by both fasting hyperglycemia and exaggerated postprandial increases in plasma glucose levels. NIDDM is associated with a variety of long-term complications, including microvascular diseases such as retinopathy, nephropathy and neuropathy, and macrovascular diseases such as coronary heart disease. Numerous studies in animal models demonstrate a causal relationship between long term hyperglycemia and complications. Results from the Diabetes Control and Complications Trial (DCCT) and the Stockholm Prospective Study demonstrate this relationship for the first time in man by showing that insulin-dependent diabetics with tighter glycemic control are at substantially lower risk for the development and progression of these complications. Tighter control is also expected to benefit NIDDM patients.

Current therapies used to treat NIDDM patients entail both controlling lifestyle risk factors and pharmaceutical intervention. First-line therapy for NIDDM is typically a tightly-controlled regimen of diet and exercise since an overwhelming number of NIDDM patients are overweight or obese (67%) and since weight loss can improve insulin secretion, insulin sensitivity and lead to normoglycemia. Normalization of blood glucose occurs in less than 30% of these patients due to poor compliance and poor response.

Over the years, significant effort has been brought to bear towards developing inhibitors against fructose-1,6-bisphosphatase (FBPase), as novel therapeutics for the treatment of type-2 diabetes. Inhibitors have been searched for because FBPase is a critical enzyme involved in the control of gluconeogenesis.[1,2] In type-2 diabetes, the enzymatic control of the gluconeogenesis pathway is compromised, thus allowing the production of excessive amounts of glucose resulting in the elevated blood glucose levels characteristic of the disease. In normal individuals, when blood glucose levels are high there is a corresponding increase in the concentration of fructose 2,6-bisphosphate, a highly potent competitive inhibitor of FBPase. The activity of FBPase can also be inhibited allosterically by AMP, thus providing alternate sites for the development of potent therapeutics.

FBPase is a homotetrameric enzyme that exists in either an active (R) or an inactive (T) conformational state.[3] Regulation of enzymatic activity involves changes in conformation of the quaternary structure between the R and T states. Metal cations, fructose 1,6-bisphosphate, and fructose-6-phosphate stabilize the R state, while AMP acts as the negative allosteric regulator of FBPase activity, inducing the conformational change from the R to T state. It has also been found that fructose-2,6-bisphosphate synergistically increases the binding of AMP.[2]

As a drug target, there are three possible sites of inhibition: the active site, which binds the substrate fructose-1,6-bisphosphate (FBP), the allosteric site which binds AMP, and a 'novel allosteric site', at the intersection of the two-fold axis.

To date, considerable research has been focused on designing small molecule inhibitors of FBPase. In 2001, Wright et al.[4] reported a novel series of anilinoquinazolines as allosteric inhibitors of FBPase. These inhibitors were identified through screening a library of compounds known to be enzyme inhibitors that compete with AMP and/or ATP, and they were eventually found to bind at the 'novel allosteric site'. Other small-molecule inhibitors include MB05032.[5] The actual drug candidate, CS-917, is a pro-drug version of MB05032, in which the charged phosphate is protected by groups that are removed in vivo.[5] MB05032 binds to the allosteric site of human FBPase and is competitive with the binding of AMP. Another class of inhibitors identified by a high-throughput screen (HTS) is a group of benzoxazole-2-benzenesulfonamides reported by Geldern et al.[6]

Millions of people have Type 2 diabetes. Efforts are underway by various groups to develop small molecule compounds that can help to combat this disease. Many different targets have been identified and many different approaches are being investigated. Since the enzyme FBPase naturally controls the formation of sugar, it has been a target for the development of anti-diabetic drugs. However, most of these possible drug candidates have not been successfully passed through all of the stages of drug testing.

There is thus an ongoing need to create new compounds that can be used to fight diabetes. This invention answers that need.

SUMMARY OF THE INVENTION

The invention is directed to compounds according to formula (I) or to pharmaceutical compositions comprising an effective amount of a compound according to formula (I):

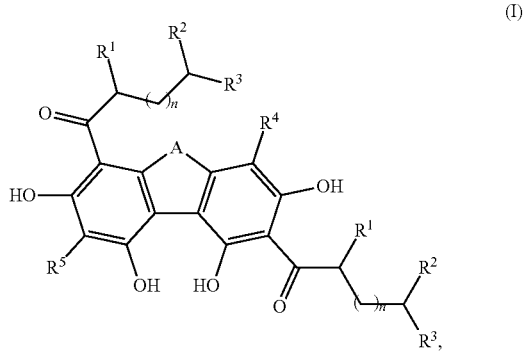

or prodrugs, pharmaceutically acceptable salts, stereoisomer mixtures, and enantiomers thereof.

In formula (I), A may represent oxygen, $CH_2$, sulfur, NH or, $NCH_3$. $R^1$, $R^2$, and $R^3$ may each independently represent hydrogen, halogen, branched or unbranched, substituted or unsubstituted $C_1$-$C_6$ alkyl, $C_2$-$C_6$ alkenyl, $C_2$-$C_6$ alkynyl, alcohol, alkoxy, aryloxy, aryl, alkylaryl, alkoxyaryl, epoxide, —COOH, —CN, —$CX_3$, —$C(O)R^6$, —$C(O)N(R^6)_2$, —C=C=$C(R^6)_2$, —OH, —OAc, —$OC(O)R^6$, —$SO_3$, —$S(O)_2R^6$, —$S(R^6)$, —SAc, —NHC(O)Ar, —$NHCH_2Ar$, —$N(R^6)_2$, —N=$N(R^6)$, —$SiH_3$, —$P(O)(X)_2$, —$P(O)(OR^6)_2$, —$P(R^6)_2$, —$OPO_3$,

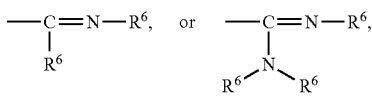

where X is a halogen, Ac is acetyl, and Ar is an aryl group, and wherein each $R^6$ is independently H or $C_1$-$C_4$ alkyl. $R^4$ and $R^5$ may each represent hydrogen, halogen, a substituted or unsubstituted $C_1$-$C_6$ alkyl, —OH, —COOH, —CN, —$N(R^6)_2$, —$NO_2$, or —$S(R^6)$, where each $R^6$ is independently H or $C_1$-$C_4$ alkyl. The variable "n" represents an integer from 0-5.

Another aspect of the invention is directed to methods for treating diabetes or diabetes-related disorders. The methods include selecting a subject in need of treatment for diabetes and administering to the subject a compound of formula (I) substantially as those described above.

Another aspect of the invention is directed to methods for inhibiting fructose-1,6-bisphosphatase (FBPase). The methods include contacting FBPase with a compound of formula (I) or a pharmaceutical composition of formula (I), each substantially as those described above, under conditions effective to inhibit said FBPase.

DETAILED DESCRIPTION OF THE INVENTION

Figure 1A:
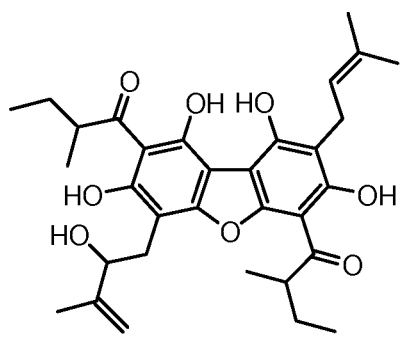
FIG. 1 shows the structural formulas of (FIG. 1A) achyrofuran (1) and (+)-usnic acid (2), and FIG. 1B) two exemplary compounds of the invention.
Figure 1A:
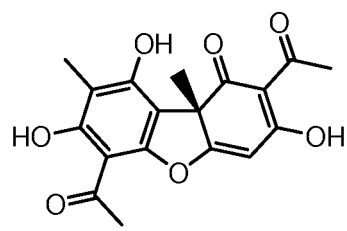
Figure 1B:
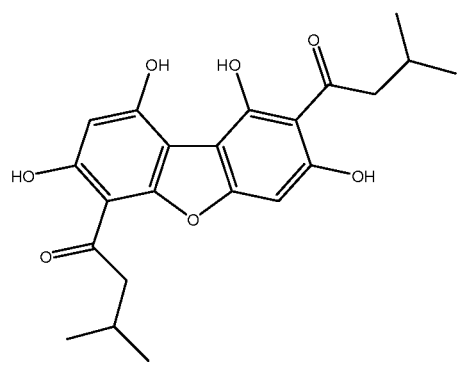
Figure 1B:
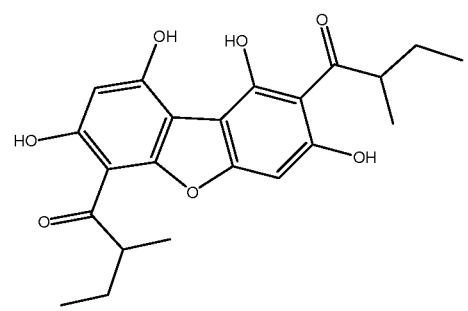

FBPase is a critical enzyme involved in the control of gluconeogenesis. In patients suffering with type-2 diabetes, enzymatic control of the gluconeogenesis pathway is compromised. Excessive amounts of glucose are produced resulting in the elevated blood glucose levels characteristic of the disease. In normal individuals, when blood glucose levels are high there is a corresponding increase in the concentration of fructose 2,6-bisphosphate, a highly potent competitive inhibitor of FBPase. Certain patients stand to benefit from inhibition of the activity of FBPase alone or in combination with other therapeutic agents to treat diabetes. It has been found that the compounds and pharmaceutical compositions of the present invention inhibit the activity of FBPase and, thereby, help control gluconeogenesis.

A series of chemical compounds has therefore been developed that bind to the enzyme fructose 1,6-bisphosphatase (FBPase). The new class of inhibitors is based on the modification of achyrofuran, a natural product obtained from Achyrocline satureoides. *Achyrocline satureoides* is a medium-sized aromatic herb that grows throughout Brazil, Uruguay and Argentina and is known by the name of "macela." Macela has been used in herbal medicine for many years for a variety of ailments including the treatment of type-2-diabetes throughout the region where it grows naturally. However, it was not until 2002 that researchers validated this use. Carney et al.[9] isolated a dibenzofuran derivative, achyrofuran, from the plant *Achyrocline satureioides*, using a bioassay-guided fractionation based on a diabetic db/db mouse model. Although Carney et al.[9] established that achyrofuran was the active component in *A. satureioides* responsible for its anti-hyperglycemic ability, the in vivo target was not identified.

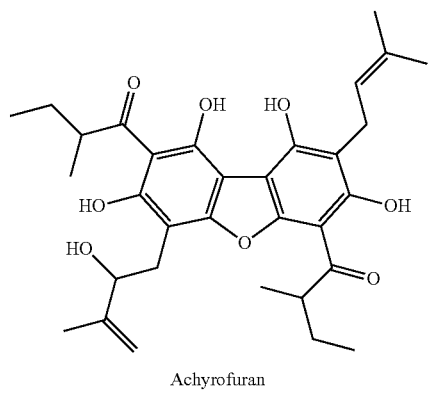 [SMILES: C=C(C)C(O)Cc1c(O)c(C(=O)C(C)CC)c(O)c2c1oc1c(C(=O)C(C)CC)c(O)c(CC=C(C)C)c(O)c12]

Achyrofuran

The compounds of this invention represent a new class of drugs that can be used in methods of treating patients suffering from type-2-diabetes. The invention is directed to compounds according to formula (I):

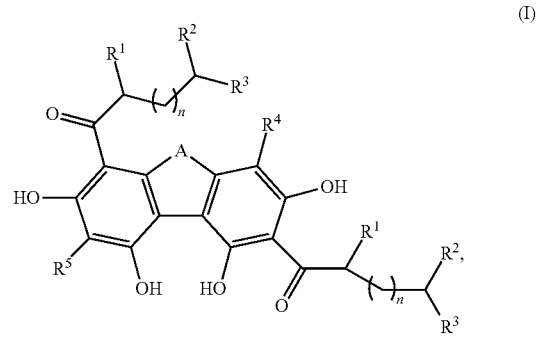

(I)

or prodrugs, pharmaceutically acceptable salts, stereoisomer mixtures, and enantiomers thereof.

In formula (I), A may represent oxygen, $CH_2$, sulfur, NH or, $NCH_3$. Preferably, A represents oxygen.

$R^1$, $R^2$, and $R^3$ may each independently represent hydrogen, halogen, branched or unbranched, substituted or unsubstituted $C_1$-$C_6$ alkyl, $C_2$-$C_6$ alkenyl, $C_2$-$C_6$ alkynyl, alcohol, alkoxy, aryloxy, aryl, alkylaryl, alkoxyaryl, epoxide, —COOH, —CN, —$CX_3$, —$C(O)R^6$, —$C(O)N(R^6)_2$, —C=C=$C(R^6)_2$, —OH, —OAc, —$OC(O)R^6$, —$SO_3$, —$S(O)_2R^6$, —$S(R^6)$, —SAc, —NHC(O)Ar, —$NHCH_2Ar$, —$N(R^6)_2$, —N=$N(R^6)$, —$SiH_3$, —$P(O)(X)_2$, —$P(O)(OR^6)_2$, —$P(R^6)_2$, —$OPO_3$,

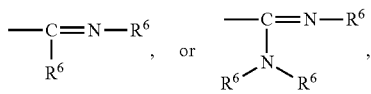

where X is a halogen, Ac is acetyl, and Ar is an aryl group, and wherein each $R^6$ is independently H or $C_1$-$C_4$ alkyl.

Preferably, $R^1$, $R^2$, and $R^3$ each independently represent methyl, i-butyl, —OCH$_2$Ph, hydrogen, ethyl, t-butyl, —F, —SH, n-propyl, phenyl, —Cl, —SCH$_3$, i-propyl, methoxy, —Br, —SAc, ethoxy, —I, —SiH$_3$, n-butyl, —OPh, —OH, —NH$_2$, —COOH, —OAc, epoxy, —CF$_3$, —C(O)N(CH$^3$)$_2$, —CH=CH$_2$, —SO$_3$, —C(O)H, —NHC(O)Ph, —C≡CH, —C(O)NHCH$_3$, —NHCH$_2$Ph, —oPO$_3$, —OC(O)H, —P(O)(Cl)$_2$, —P(O)(OCH$_2$CH$_3$)$_2$, —P(O)(OCH$_3$)$_2$, —P(O)(OH)$_2$, —CH$_2$OH, —N=N—CH$_3$, —S(O)$_2$CH$_3$, —C(O)CH$_3$, —C=C=C(CH$_2$)$_2$, —CN, —P(CH$_3$)$_2$,

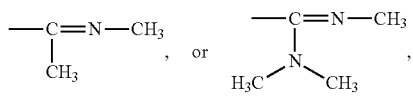

where Ph is phenyl and Ac is acetyl. Most preferably, $R^1$, $R^2$, and $R^3$ are each independently hydrogen or $C_1$-$C_6$ alkyl.

$R^4$ and $R^5$ may each represent hydrogen, halogen, a substituted or unsubstituted $C_1$-$C_6$ alkyl, —OH, —COOH, —CN, —N(R$^6$)$_2$, —NO$_2$, or —S(R$^6$), where each $R^6$ is independently H or $C_1$-$C_4$ alkyl. Preferably, $R^4$ and $R^5$ are each independently selected from the group consisting of hydrogen, halogen, methyl, —OH, —COOH, —CN, —NH$_2$—N(CH$_3$)$_2$, —NO$_2$, —SH, and —SCH$_3$. Most preferably, $R^4$ and $R^5$ are each hydrogen.

The variable "n" represents an integer from 0-5. Preferably, n is 0.

Preferably the compound of formula (I) is not achyrofuran or 1,1'-(1,3,7,9-tetrahydroxy-2,6-dimethyldibenzofuran-4,8-diyl)-di-(3-methyl)-butan-1-one.

In a preferred embodiment of the invention, $R^1$ is hydrogen, $R^2$ is methyl, and $R^3$ is methyl, $R^4$ is hydrogen, $R^5$ is hydrogen, and n is 0, Such a structure is represented by formula (II), below:

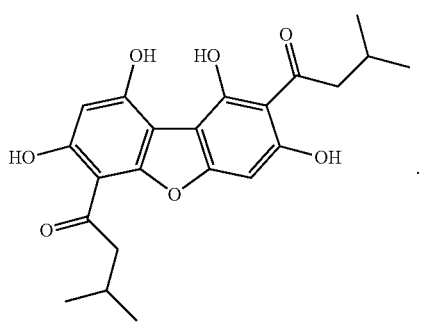

In another preferred embodiment of the invention, R is methyl, R is hydrogen, and $R^3$ is methyl, $R^4$ is hydrogen, $R^5$ is hydrogen, and n is 0, Such a structure is represented by formula (III), below:

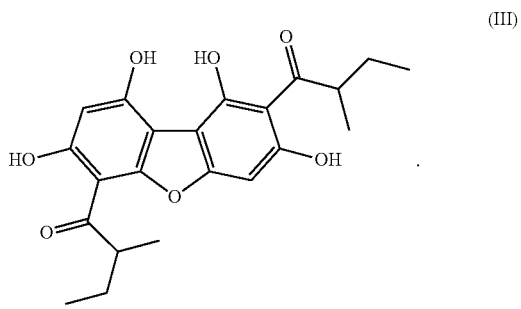 [SMILES: CCC(C)C(=O)c1c(O)cc2oc3c(C(=O)C(C)CC)c(O)cc(O)c3c2c1O]

The compounds of formula (I) include prodrugs, pharmaceutically acceptable salts, stereoisomer mixtures, and enantiomers thereof. The compounds of the invention also include pharmaceutically acceptable salts of the compounds of formula (I). Preferred pharmaceutically acceptable salts are physiologically acid-addition salts. Common pharmaceutically acceptable acid-addition salts include but are not limited to, hydrochloric acid salts, oxalate salts, and tartrate salts.

The term "prodrug" as used herein refers to compounds that can be converted via some chemical or physiological process (e.g., enzymatic processes and metabolic hydrolysis) to a compound described herein. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, carboxyl, amino or mercapto group is bonded to any group that, when the prodrug of the active compound is administered to a subject, cleaves to form a free hydroxy, free carboxyl, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design*, Theory and Application, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bio-precursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenyloin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *I. Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *I. Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), contents of all of which are herein incorporated by reference in its entirety.

The compounds of the invention may be prepared according to a general synthetic procedure. The examples below demonstrate the general synthetic procedure, as well as the specific preparation, for compounds according to this invention. The examples are illustrative, and are not intended to limit, in any manner, the claimed invention.

The compounds of this invention, useful as inhibitors of FBPase, can be synthesized in large quantities and their structures can easily be modified to provide a variety of alternative structures that may produce drugs with more useful characteristics. This is particularly advantageous, as achyrofuran can be isolated only in extremely small quantities from the plant Achyrocline satureoides. For instances, studies have reported that only 3.8 mg of achyrofuran was isolated from 6 kg of whole plant material (yield 0.00023%). Using the synthetic route set forth below, the compounds of the invention were synthesized with much higher overall yield, beginning from commercial available starting materials.

Yet another aspect of the invention is directed to methods for treating diabetes and related diabetes disorders. The methods include selecting a subject in need of treatment for diabetes or related diabetes disorders and administering to the subject a compound of formula (I) substantially as those described above. Suitable subjects include mammals, such as humans. The methods also include selecting a subject in need of treatment for diabetes and related diabetes disorders and administering to the subject a pharmaceutical composition of formula (I) substantially as those described above.

The compounds of formulas (II) and (III) are particularly preferred for use with these methods. As set forth below in the examples, both of these compounds were found to inhibit both human liver and pig kidney FBPase at values that are comparable to that of AMP, the natural allosteric inhibitor of this enzyme.

Diabetes and related diabetes disorders include, but are not limited to, the following disorders: Type 1 diabetes, Type 2 diabetes, maturity-onset diabetes of the young (MODY), latent autoimmune diabetes adult (LADA), impaired glucose tolerance (IGT), impaired fasting glucose (IFG), gestational diabetes, and metabolic syndrome X. In a preferred embodiment, the method is used to treat Type 1 or Type 2 diabetes.

The natural product, achyrofuran, was able to lower plasma glucose levels better than that of Metformin (250 mg/kg) and has been shown to possess no apparent acute toxic effect at the dose level of only 20 mg/kg. While the possible anti-diabetic properties has been investigated, the in vivo target is not known. By using the target of FBPase as a guide, the design and testing of new agents can be accomplished in vitro before in vivo testing is required. In this fashion, the structure of new more effective agents can be rapidly prototyped. This represents a significant advantage for the compounds of this invention.

Typical administration times within one hour before or after a meal, when monitored blood sugar levels are found to be high or symptoms of hyperglycemia or diabetic ketoacidosis are present, or as directed by a prescribing physician. Other administrations times may also be suitable. Administration may be in response to results obtained by monitoring of blood sugar levels by methods known in the art or in response to symptoms of hyperglycemia or diabetic ketoacidosis. The patient's doctor will determine the patients target blood sugar range. For many people who have diabetes, target levels are:

Before meals—between 90 and 130 milligrams per deciliter (mg/dL), or 5 and 7 millimoles per liter (mmol/L), also known as fasting blood sugar level;

One to two hours after meals—lower than 180 mg/dL (10 mmol/L);

Before bedtime—between 110 and 150 mg/dL (6 and 8 mmol/L).

Effective dosage amounts range from 0.01 to 250 mg/kg of the compound. In certain embodiments, the effective dose comprises 0.01 to 100 mg/kg of the compound.

The effective dosage may be determined by a physician and adjusted, as necessary, to suit observed effects of the treatment. Generally, the compositions are administered so that the dose comprises from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg of the compound. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

The compounds described above can either be administered alone, in the form of mixtures with one another, or in combination with acceptable pharmaceutical carriers. The invention, thus, also relates to pharmaceutical compositions which comprise an effective amount of at least one compound of the invention with or without a pharmaceutically or physiologically acceptable carrier. If appropriate, the compound may be administered in the form of a physiologically acceptable salt, for example, an acid-addition salt.

The invention also encompasses a method of treating animals or humans. This method comprises administering to the animal or humans an effective amount of at least one of the compounds of the invention, or a physiologically acceptable salt thereof, with, or without a pharmaceutically acceptable carrier.

The term "effective amount" refers to a dosage or amount that is sufficient to ameliorate clinical symptoms of, or achieve a desired biological outcome in individuals suffering from diabetes. The term "therapeutic agent" is a substance that treats or assists in treating a medical disorder.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques.

Intraarterial and intravenous injection as used herein includes administration through catheters. Oral administration is generally preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethyl cellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives.

Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Compounds of the invention may be administered as a daily dose or an appropriate fraction of the daily dose (e.g. bid). Administration of the FBPase inhibitor may occur alone or in combination with one or more insulin sensitizers. Administration of the FBPase inhibitor may occur at or near the time in which the insulin sensitizer active ingredient is administered or at a different time. Simultaneous administration of the active ingredients is achieved either by administration of the active ingredients in the same or different formulations. Formulations include time-release formulations intended to release either both of the active ingredients simultaneously or to stage the release of the active ingredients such that release, absorption and systemic exposure occurs with one of the ingredients before the other.

The amount of active ingredient that may be combined with the carrier material to produce a single dosage form will vary depending upon the host treated and the particular mode of administration. Generally out of one hundred percent, this amount will range from about 0.1% to 99% of the active ingredient, preferably from about 5% to about 95%. For example, a formulation intended for oral administration to humans may contain 20 to 2000 μmol (approximately 10 to 1000 mg) of active material compounded with an appropriate and convenient amount of carrier material which may vary from about 5 to about 95% of the total compositions.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the 1050 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

As noted above, formulations of the present invention suitable for oral administration may be presented as discrete units such as capsules, cachets or tablets each containing a predetermined amount of the active ingredient; as a powder or granules; as a solution or a suspension in an aqueous or nonaqueous liquid; or as an oil-in-water liquid emulsion or a water in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier. Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate. Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, or an appropriate fraction thereof, a fructose-1,6-bisphosphatase inhibitor compound or a fructose-1,6-bisphosphatase inhibitor compound and an insulin sensitizer.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Capsules comprising FBPase inhibitors suitable for oral administration according to the methods of the present invention may be prepared as follows: (1) for a 10,000 capsule preparation: up to 5000 g of FBPase inhibitor is blended with other ingredients (as described above) and filled into capsules which are suitable for administration depending on dose, from about 1 capsules per day to about 8 capsules per day (2 capsules per 6 hours), to an adult human.

Capsules comprising insulin sensitizers suitable for oral administration according to the methods of the present invention may be prepared as follows: (1) for a 10,000 capsule preparation: up to 5000 g of insulin sensitizer is blended with other ingredients (as described above) and filled into capsules which are suitable for administration depending on dose, from about 1 capsules per day to about 8 capsules per day (2 capsules per 6 hours), to an adult human.

Capsules comprising FBPase inhibitors and insulin sensitizers suitable for oral administration according to the methods of the present invention may be prepared as follows: (1) for a 10,000 capsule preparation: up to 2500 g of FBPase inhibitor and up to 2500 g of insulin sensitizer are blended with other ingredients (as described above) and filled into capsules which are suitable for administration depending on dose, from about 1 capsules per day to about 8 capsules per day (2 capsules per 6 hours), to an adult human.

Other therapeutic agents known in the art may by used in combination with the compounds of the present invention. Exemplary therapeutic agents include, but are not limited to, those found in *Harrison's Principles of Internal Medicine*, 13$^{th}$ Edition, Eds. T. R. Harrison et al. McGraw-Hill N.Y., N.Y.; Physicians Desk Reference, 50$^{th}$ Edition, 1997, Oradell New Jersey, Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of The Merck Index, the complete contents of all of which are incorporated herein by reference. In some embodiments the therapeutic agent is an agent known in the art for treating diabetes or related disorders.

Insulins useful with the methods and combinations of this invention include rapid acting insulins, intermediate acting insulins, long acting insulins and combinations of intermediate and rapid acting insulins. Insulin therapy replaces insulin that is not being produced by the body. The combination of a rapid- or short-acting and intermediate- or long-acting insulin helps keep blood sugar levels within normal or closer to normal levels. The use of these agents is described in further detail in U.S. Patent Pub. No. 2002/0187980-A1 (application Ser. No. 10/164,235), relevant portions thereof are herein incorporated by reference.

Rapid acting commercially available insulin products include the HUMALOG® Brand Lispro Injection (rDNA origin), HUMULIN® R Regular Human Injection, USP [rDNA origin], HUMULIN® R Regular U-500 Concentrated Human Injection, USP [rDNA origin], REGULAR ILETIN® II (insulin injection, USP, purified pork) available from Eli Lilly and Co., and the NOVOLIN® Human Insulin Injection and VENOSULIN® BR Buffered Regular Human Injection, each available from Novo Nordisk Pharmaceuticals.

Commercially available intermediate acting insulins useful with this invention include, but are not limited to, the HUMULIN® L brand LENTE® human insulin (recombinant DNA origin) zinc suspension, HUMULIN® N NPH human insulin (recombinant DNA origin) isophane suspension, LENTE® ILETIN® II insulin zinc suspension, USP, purified pork, and NPH ILETIN® II isophane insulin suspension, USP, purified pork, available from Eli Lilly and Company, LANTUS® insulin glargine (recombinant DNA origin) injection, available from Aventis Pharmaceuticals, and the NOVOLIN L Lente® human insulin zinc suspension (recombinant DNA origin), and NOVOLIN® N NPH human insulin isophane suspension (recombinant DNA origin) products available from Novo Nordisk Pharmaceuticals, Inc, Princeton N.J.

Also useful with the methods and formulations of this invention are intermediate and rapid acting insulin combinations, such as the HUMALOG® Mix 75/25® (75% Insulin Lispro Protamine Suspension and 25% Insulin Lispro Injection), HUMULIN® 50/50 (50% Human Insulin Isophane Suspension and 50% Human Insulin Injection) and HUMULIN® 70/30® (70% Human Insulin Isophane Suspension and 30% Human Insulin Injection), each available from Eli Lilly and Company. Also useful are the NOVALIN® 70/30 (70% NPH, Human Insulin Isophane Suspension and 30% Regular, Human Insulin Injection) line of combination products, which are intermediate and rapid acting insulin available from Novo Nordisk Pharmaceuticals.

An exemplary commercially available long acting insulin for use with this invention is the HUMULIN® U Ultralente® human insulin (recombinant DNA origin) extended zinc suspension, available from Eli Lilly and Company.

Also useful in the methods of this invention are inhaled insulin products, such as the EXUBERA® inhaled insulin product developed by Pfizer Inc. and Aventis SA.

Each of these insulin products can be administered as directed by a medical professional using administrations, dosages and regimens known in the art, such as those published for each product in the Physicians' Desk Reference, 55 Edition, 2001, published by Medical Economics Company, Inc. at Montvale, N.J., the relevant sections of which are incorporated herein by reference.

Sulfonylurea agents increase the amount of insulin produced by the pancreas. They also increase the effectiveness of insulin throughout the body by increasing functionality of insulin receptors and stimulating the production of more insulin receptors. These agents also reduce insulin resistance and may reduce the amount of sugar made by the liver.

Sulfonylurea agents useful with the methods and compositions of this invention include glipizide, glyburide (glibenclamide), chlorpropamide, tolbutamide, tolazamide and glimepriride, or the pharmaceutically acceptable salt forms thereof. The use of these agents are described in further detail in U.S. Patent Pub. No. 2003/008869-A1 (application Ser. No. 10/163,783), relevant portions of which are herein incorporated by reference.

The sulfonylurea agents of this invention may be administered at doses and regimens known in the art, such as those listed for the relevant compounds in the Physicians' Desk Reference, 55 Edition, 2001, published by Medical Economics Company, Inc. at Montvale, N.J. For example, glimepiride, which is available in AMARYL® tablets from Aventis Pharmaceuticals, may be given at an initial daily dosage of from about 1 to about 2 mg per day in human adults. This dosage may be increased gradually up to about 8 mg per day, with a usual maintenance dose being between about 2 and 4 mg per day. Glyburide is available in DIAβETA® tablets from Aventis Pharmaceuticals, and has an initial dose ranging from about 2.5 to about 5 mg per day and a usual maintenance dose of from about 1.25 to about 20 mg per day. Chlorpropamide is available from Pfizer Inc. in DIABINESE®tablets, and may have a daily dose in humans of from about 100 to about 500 mg, depending upon the individual characteristics of the recipient. Glipizide is commercially available in GLUCOTROL® tablets and GLUCOTROL XL® extended release tablets from Pfizer Inc. It can be administered at an initial daily dose of from about 2.5 to about 5 mg and increased in 2.5 to 5 mg increments to a maintenance dose of between about 15 and 40 mg per day. Tolazamide is generally administered at a daily dosage of between about 100 mg and 500 mg per day, with an average maintenance dose of between about 250 mg and 500 mg per day taken once daily or divided into multiple administrations over the course of a day. 250 mg and 500 mg tablets of tolazamide and 500 mg tablets of tolbutamide are available from Mylan Pharmaceuticals Inc., Morgantown, W.Va., U.S.A.

Biguanide agents lower blood sugar by decreasing the amount of sugar produced by the liver in gluconeogenesis. They also increase the amount of sugar absorbed by muscle cells and decrease insulin resistance. These agents may lower triglyceride levels in the blood and reduce certain abnormal clotting factors and markers of inflammation that can lead to atherosclerosis. Biguanide agents useful with the methods and compositions of this invention include metformin and its pharmaceutically acceptable salt forms. The use of these agents is described in further detail in U.S. Patent Pub. No. 2003/0018028-A1 (application Ser. No. 10/163,707), relevant portions thereof are herein incorporated by reference.

Metformin hydrochloride useful in the methods and combinations is commercially available in 500 mg, 850 mg and 1000 mg tablets under the GLUCOPHAGE® tradename from Bristol Myers Squibb. Metformin hydrochloride may be administered in humans at an initial daily dose of from 500 mg to about 800 mg and increased, as needed, to a maximum daily dosage of 2550 mg.

Thiazolidinedione agents improve the way cells in the body respond to insulin by lowering insulin resistance. They also may help in the treatment of high cholesterol by reducing triglycerides and increasing high-density lipoproteins (HDL) in the blood.

Thiazolidinedione agents useful with the methods and compositions of this invention are the non-limiting group of pioglitazone or rosiglitazone, or a pharmaceutically acceptable salt form of these agents. The use of these agents is described in further detail in U.S. Patent Pub. No. 2002/0198203-A1 (application Ser. No. 10/164,233), relevant portions thereof are herein incorporated by reference. Each of these agents may be produced by methods known in the art. These agents may also be administered at the pharmaceutically or therapeutically effective dosages or amounts known in the art for these compounds, such as those described in the Physician's Desk Reference 2001, 55 Edition, Copyright 2001, published by Medical Economics Company, Inc., the relevant portions describing each of these products being incorporated herein by reference.

Pioglitazone is available in the form of 15 mg, 30 mg and 45 mg ACTOS® brand pioglitazone hydrochloride tablets from Swiss Bioceutical International, Ltd. Pioglitazone and its pharmaceutically acceptable salt forms may be administered in humans at an initial daily dose of from about 15 mg or 30 mg and increased, as needed, to a maximum daily dose of about 45 mg.

Rosiglitazone is available in the form of 2 mg, 4 mg and 8 mg AVANDIA® rosiglitazone maleate tablets from GlaxoSmithKline. Rosiglitazone may be administered in humans at an initial daily dose of about 4 mg in a single or divided doses and increased, as needed, up to a maximum daily dose of 8 mg.

Alpha-glucosidase inhibitors delay the digestion of carbohydrates in the body and slow the rate at which the intestines absorb glucose from food. This decreases the amount of sugar that passes into your blood after a meal and prevents periods of hyperglycemia. Alpha-glucosidase inhibitors which may be used with the methods and compositions of the invention described herein are miglitol or acarbose, or a pharmaceutically acceptable salt form of one or more of these compounds.

The use of these agents is described in further detail in U.S. Patent Pub. No. 2003/0013709-A1 (application Ser. No. 10/164,232), relevant portions thereof are herein incorporated by reference.

Acarbose tablets are available from Bayer Corporation under the PRECOSE® tradename, which may be administered in humans at an initial dose of about 25 mg administered from one to three times daily and increased over time to a range of from about 50 to 100 mg administered three times per day.

Miglitol tablets in 25 mg, 50 mg and 100 mg doses are available under the GLYSET® tradename from Pharmacia & Upjohn and may be administered at an initial dose of about 25 mg per day and increased as needed to a maximum dose of 100 mg administered three times daily.

Protein tyrosine phosphatases (PTPases) are a large family of diverse molecules that can play an important role in modulating a wide variety of cellular responses. The PTPase family is divided into three major subclasses, classical PTPases, low molecular weight PTPases, and dual specificity PTPases. The classical PTPases can be further categorized into two classes, intracellular PTPases (e.g., PTP1B, TC-PTP, rat-brain PTPase, STEP, PTPMEG1, PTPH1, PTPD1, PTPD2, FAP-1/BAS, PTP1C/SH-PTP1/SHP-1 and PTP1D/S/SH-PTP2/SHP2) and receptor-type PTPases (e.g., CD45, LAR, PTP1, PTP1, PTPA, PTPM, PTPK, SAP-1 and DEP-1). Dual specificity phosphatases have the ability to remove the phosphate group from both serine/threonine and tyrosine residues. Members of the PTPase family have been implicated as important modulators or regulators of a wide variety of cellular processes including insulin signaling, leptin signaling, T-cell activation and T-cell mediated signaling cascade, the growth of fibroblasts, platelet aggregation, and regulation of osteoblast proliferation.

Certain PTPase inhibitors are described in detail in U.S. Patent Application Nos. 60/547,071 and 60/547,049, relevant portions of which are herein incorporated by reference. Other PTPase inhibitors may be used in this invention as well.

Effective administration of these compounds may be given at a daily dosage of from about 1 mg/kg to about 250 mg/kg, for example, and may be given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

In combination therapy methods described herein, at least one compound of the present invention is administered with at least one other therapeutic agent as provided above. The combination therapy may also include a combination of more than one compound of the present invention and/or more than one therapeutic agents.

As with the monotherapy, the combination therapy can be administered simultaneously or sequentially. Simultaneous administration requires the administration of at least one dose of each of the compound of the present invention and at least one therapeutic agent at the same time or times. Sequential administration may include a bolus dosage of the compound of the present invention followed by multiple doses of at least one therapeutic agent over time; it may also include multiple doses of both compounds. Varying the dosage pattern may vary the results in achieving the desired treatment goal.

Another aspect of the invention is directed to methods for inhibiting fructose-1,6-bisphosphatase (FBPase). The methods include contacting FBPase with a compound of formula (I) or a pharmaceutical composition of formula (I), each substantially as those described above, under conditions effective to inhibit said FBPase.

For contacting with a compound, the FBPase can be purified, e.g. from a cell producing the FBPase, before contacting or FBPase can still be in the cell that produces the FBPase. When the FBPase is in a cell, the compound can be contacted with the cell in a cell culture e.g., in vitro, or the compound can be administered to a subject, e.g., in vivo. In some embodiments of the invention, a compound described herein can be administered to a subject to treat, and/or prevent diabetes or related disorders.

The term "contacting" or "contact" as used herein in connection with contacting a cell includes subjecting the cell to an appropriate culture media which comprises the indicated compound. Where the cell is in vivo, "contacting" or "contact" includes administering the compound in a pharmaceutical composition to a subject via an appropriate administration route such that the compound contacts the cell in vivo. For in vivo methods, a therapeutically effective amount of a compound described herein can be administered to a subject.

The compounds of the present invention can be administered orally, parenterally, for example, subcutaneously, intravenously, intramuscularly, intraperitoneally, by intranasal instillation, by inhalation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The compounds of the present invention may also be administered directly to the airways in the form of a dry powder. For use as a dry powder, the compounds of the present invention may be administered by use of an inhaler. Exemplary inhalers include metered dose inhalers and dry powdered inhalers. A metered dose inhaler or "MDI" is a pressure resistant canister or container filled with a product such as a pharmaceutical composition dissolved in a liquefied propellant or micronized particles suspended in a liquefied propellant. The correct dosage of the composition is delivered to the patient. A dry powder inhaler is a system operable with a source of pressurized air to produce dry powder particles of a pharmaceutical composition that is compacted into a very small volume. For inhalation, the system has a plurality of chambers or blisters each containing a single dose of the pharmaceutical composition and a select element for releasing a single dose.

Suitable powder compositions include, by way of illustration, powdered preparations of the active ingredients thoroughly intermixed with lactose, or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation. The compositions can include propellants, surfactants, and co-solvents and may be filled into conventional aerosol containers that are closed by a suitable metering valve.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to compounds. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "aryloxy", "aryl", "heteroaryl", "heterocyclic", "alkyl" "alkenyl", "alkynyl", or "cycloalkyl", those skilled in the art will understand that the terms "alkoxy", "aryloxy", "aryl", "heteroaryl", "heterocyclic", "alkyl", "alkenyl", "alkynyl", or "cycloalkyl" refer to the corresponding divalent moiety.

The term "halo" refers to any radical of fluorine, chlorine, bromine or iodine.

The term "acyl" refers to an alkylcarbonyl, cycloalkylcarbonyl, arylcarbonyl, heterocyclylcarbonyl, or heteroarylcarbonyl substituent, any of which may be further substituted by substituents. Exemplary acyl groups include, but are not limited to, ($C_1$-$C_6$)alkanoyl such as formyl, acetyl, propionyl, butyryl, valeryl, caproyl, and t-butylacetyl.

The term "alkyl" refers to saturated non-aromatic hydrocarbon chains that may be a straight chain or branched chain, containing the indicated number of carbon atoms (these include without limitation methyl, ethyl, propyl, allyl, or propargyl), which may be optionally inserted with N, O, or S. For example, $C_1$-$C_6$ indicates that the group may have from 1 to 6 (inclusive) carbon atoms in it.

The term "alkenyl" refers to an alkyl that comprises at least one double bond. Exemplary alkenyl groups include, but are not limited to, for example, ethenyl, propenyl, butenyl, 1-methyl-2-buten-1-yl and the like.

The term "alkynyl" refers to an alkyl that comprises at least one triple bond.

The term "alkoxy" refers to an —O-alkyl radical.

The term "aryl" refers to monocyclic, bicyclic, or tricyclic aromatic ring system wherein 0, 1, 2, 3, or 4 atoms of each ring may be substituted by a substituent. Exemplary aryl groups include, but are not limited to, phenyl, naphthyl, anthracenyl, azulenyl, fluorenyl, indanyl, indenyl, naphthyl, phenyl, tetrahydronaphthyl, and the like.

The term "alkylaryl" refers to alkyl substituted with an aryl.

The term "cyclyl" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Exemplary heterocyclyl groups include, but are not limited to piperazinyl, pyrrolidinyl, dioxanyl, morpholinyl, tetrahydrofuranyl, and the like.

The term "haloalkyl" refers to an alkyl group having one, two, three or more halogen atoms attached thereto. Exemplary haloalkyl groups include, but are not limited to chloromethyl, bromoethyl, trifluoromethyl, and the like.

The term "substituted" means that the specified group, is substituted with one or more (typically 1-4 substituents) independently selected from the group of substituents listed below in the definition for "substituents" or otherwise specified.

The term "substituents" refers to a group "substituted" on an alkyl, alkenyl, alkynyl, alcohol, alkoxy, aryloxy, cycloalkyl, heterocyclyl, heteroaryl, aryl, alkyaryl, alkoxyaryl, or epoxide group at any atom of that group. Suitable substituents include, without limitation, halo, hydroxy, oxo, nitro, haloalkyl, $C_1$-$C_6$ alkyl, $C_2$-$C_6$ alkenyl, $C_2$-$C_6$ alkynyl, alkaryl, aryl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The term "pharmaceutically acceptable salt" or "physiologically acceptable salt" refers to those salts which are, within the scope of sound medical judgment, suitable for use in contact with the tissues of humans and animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 66: 1-19, 1977; incorporated hereinby reference. The salts can be prepared in situ during the final isolation and purification of the compounds of the invention, or separately by reacting the free base functionality with a suitable organic or inorganic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of diabetes or related disorders.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

To the extent not already indicated, it will be understood by those of ordinary skill in the art that any one of the various embodiments herein described and illustrated may be further modified to incorporate features shown in any of the other embodiments disclosed herein.

The present invention may be defined in any of the following numbered paragraphs:

1. A compound according to formula (I)

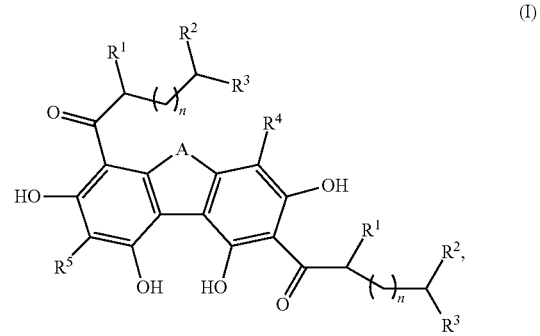

wherein,

A is oxygen, $CH_2$, sulfur, NH or, $NCH_3$;

$R^1$, $R^2$, and $R^3$ are each independently selected from the group consisting of hydrogen, halogen, branched or unbranched, substituted or unsubstituted $C_1$-$C_6$ alkyl, $C_2$-$C_6$ alkenyl, $C_2$-$C_6$ alkynyl, alcohol, alkoxy, aryloxy, aryl, alkylaryl, alkoxyaryl, epoxide, —COOH, —CN, —$CX_3$, —C(O)$R^6$, —C(O)N($R^6$)$_2$, —C=C=C($R^6$)$_2$, —OH, —OAc, —OC (O)R$^6$, —SO$_3$, —S(O)$_2$R$^6$, —S(R$^6$), —SAc, —NHC(O)Ar, —NHCH$_2$Ar, —N(R$^6$)$_2$, —N=N(R$^6$), —SiH$_3$, —P(O)(X)$_2$, —P(O)(OR$^6$)$_2$, —P(R$^6$)$_2$, —OPO$_3$, $$-\underset{R^6}{\overset{}{C}}=N-R^6 \quad \text{and} \quad -\underset{R^6\diagdown N \diagup R^6}{\overset{}{C}}=N-R^6,$$

where X is a halogen, Ac is acetyl, and Ar is an aryl group;

R$^4$ and R$^5$ are each independently selected from the group consisting of hydrogen, halogen, a substituted or unsubstituted C$_1$-C$_6$ alkyl, —OH, —COOH, —CN, —N(R$^6$)$_2$, —NO$_2$, and —S(R$^6$);

each R$^6$ is independently H or C$_1$-C$_4$ alkyl;

n is an integer from 0-5; and prodrugs, pharmaceutically acceptable salts, stereoisomer mixtures, and enantiomers thereof; and provided that compound according to formula (I) is not achyrofuran or 1,1'-(1,3,7,9-tetrahydroxy-2,6-dimethyldibenzofuran-4,8-diyl)-di-(3-methyl)-butan-1-one.

2. The compound of paragraph 1, wherein R$^1$, R$^2$, and R$^3$ are each independently selected from the group consisting of methyl, i-butyl, —OCH$_2$Ph, hydrogen, ethyl, t-butyl, —F, —SH, n-propyl, phenyl, —Cl, —SCH$_3$, i-propyl, methoxy, —Br, —SAc, ethoxy, —I, —SiH$_3$, n-butyl, —OPh, —OH, —NH$_2$, —COOH, —OAc, epoxy, —CF$_3$, —C(O)N(CH$^3$)$_2$, —CH=CH$_2$, —SO$_3$, —C(O)H, —NHC(O)Ph, —C≡CH, —C(O)NHCH$_3$, —NHCH$_2$Ph, —OPO$_3$, —OC(O)H, —P(O)(Cl)$_2$, P(O)(OCH$_2$CH$_3$)$_2$, —P(O)(OCH$_3$)$_2$, —P(O)(OH)$_2$, —CH$_2$OH, —N=N—CH$_3$, —S(O)$_2$CH$_3$, —C(O)CH$_3$, —C=C=C(CH$_2$)$_2$, —CN, —P(CH$_3$)$_2$, $$-\underset{CH_3}{\overset{}{C}}=N-CH_3 \quad \text{and} \quad -\underset{H_3C\diagdown N \diagup CH_3}{\overset{}{C}}=N-CH_3,$$

where Ph is phenyl and Ac is acetyl.

3. The compound of any of paragraphs 1-2, wherein R$^4$ and R$^5$ are each independently selected from the group consisting of hydrogen, halogen, methyl, —OH, —COOH, —CN, —NH$_2$—N(CH$_3$)$_2$, —NO$_2$, —SH, and —SCH$_3$.

4. The compound of any of paragraphs 1-3, wherein A is oxygen.

5. The compound of any of paragraphs 1-4, wherein A is oxygen; R$^1$, R$^2$, and R$^3$ are each independently hydrogen or C$_1$-C$_6$ alkyl; R$^4$ and R$^5$ are each hydrogen; and n is 0.

6. The compound of any of paragraphs 1-5, wherein R$^1$ is hydrogen, R$^2$ is methyl, and R$^3$ is methyl.

7. The compound of any of paragraphs 1-5, where R$^1$ is methyl, R$^2$ is hydrogen, and R$^3$ is methyl.

8. The compound of any of paragraphs 1-7, wherein the compound is a covalently linked with a carrier to form a prodrug.

9. A pharmaceutical composition comprising a pharmaceutically acceptable carrier and an effective amount of a compound according to any of paragraphs 1-8.

10. A method for treating diabetes or related disorders, comprising administering to a subject in need thereof a pharmaceutical composition comprising a compound of any of paragraphs 1-8.

11. The method of paragraph 10, wherein the administration step comprises administering 0.01 to 100 mg/kg of the compound.

12. The method of any of paragraphs 10-11, wherein the administration step occurs within one hour before or after a meal.

13. The method of any of paragraphs 10-13, wherein the composition further comprises an effective amount of a therapeutic agent for treatment of diabetes.

14. The method of paragraph 13, wherein the therapeutic agent is selected from the group consisting of insulin, sulfonylurea, metformin, acarbose, repaglinide, nateglinide, pioglitazone, rosiglitazone, troglitazone, exenatide, dipeptidyl peptidase (DP) IV inhibitors, and combinations thereof.

15. The method of any of paragraphs 10-14, wherein the diabetes or related disorder is Type 1 diabetes, Type 2 diabetes, maturity-onset diabetes of the young (MODY), latent autoimmune diabetes adult (LADA), impaired glucose tolerance (IGT), impaired fasting glucose (IFG), gestational diabetes, and metabolic syndrome X.

16. The method of any of paragraphs 10-15, wherein the diabetes or related disorder is Type 2 diabetes.

17. The method of any of paragraphs 10-16, wherein the pharmaceutical composition further comprises a pharmaceutically acceptable carrier.

18. A method of inhibiting fructose-1,6-bisphosphatase (FBPase) comprising: contacting FBPase with a compound of any of paragraphs 1-8 under conditions effective to inhibit said FBPase.

19. The method of paragraph 18, wherein said contact is in in vitro.

20. The method of paragraph 19, wherein said contact is in in vivo.

21. The method of paragraph 20, wherein the in vivo contact is in a mammal.

22. The method of any of paragraphs 20-21, wherein the in vivo contact is in a human.

23. The method of any of paragraphs 20-22, wherein the in vivo contact is in a subject, where the subject suffers from diabetes or related disorders.

24. The method of paragraph 23, wherein the diabetes or related disorder is Type 1 diabetes, Type 2 diabetes, maturity-onset diabetes of the young (MODY), latent autoimmune diabetes adult (LADA), impaired glucose tolerance (IGT), impaired fasting glucose (IFG), gestational diabetes, and metabolic syndrome X.

25. The method of any of paragraphs 23-24, wherein the diabetes or related disorder is Type 2 diabetes.

26. The use in the manufacture of a medicament for treating diabetes or related disorders of a composition in accordance with the formula (I):

wherein,

A is oxygen, CH$_2$, sulfur, NH or, NCH$_3$;

R$^1$, R$^2$, and R$^3$ are each independently selected from the group consisting of hydrogen, halogen, branched or unbranched, substituted or unsubstituted C$_1$-C$_6$ alkyl, $C_2$-$C_6$ alkenyl, $C_2$-$C_6$ alkynyl, alcohol, alkoxy, aryloxy, aryl, alkylaryl, alkoxyaryl, epoxide, —COOH, —CN, —CX$_3$, —C(O)R$^6$, —C(O)N(R$^6$)$_2$, —C=C=C(R$^6$)$_2$, —OH, —OAc, —OC(O)R$^6$, —SO$_3$, —S(O)$_2$R$^6$, —S(R$^6$), —SAc, —NHC(O)Ar, —NHCH$_2$Ar, —N(R$^6$)$_2$, —N=N(R$^6$), —SiH$_3$, —P(O)(X)$_2$, —P(O)(OR$^6$)$_2$, —P(R$^6$)$_2$, —OPO$_3$,

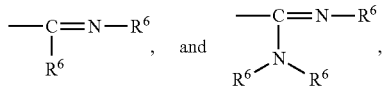

where X is a halogen, Ac is acetyl, and Ar is an aryl group;
R$^4$ and R$^5$ are each independently selected from the group consisting of hydrogen, halogen, a substituted or unsubstituted $C_1$-$C_6$ alkyl, —OH, —COOH, —CN, —N(R$^6$)$_2$, —NO$_2$, and —S(R$^6$);
each R$^6$ is independently H or $C_1$-$C_4$ alkyl;
n is an integer from 0-5; and
prodrugs, pharmaceutically acceptable salts, stereoisomer mixtures, and enantiomers thereof; and provided that compound according to formula (I) is not achyrofuran or 1,1'-(1,3,7,9-tetrahydroxy-2,6-dimethyldibenzofuran-4,8-diyl)-di-(3-methyl)-butan-1-one.

27. The use of paragraph 26, wherein R$^1$, R$^2$, and R$^3$ are each independently selected from the group consisting of methyl, i-butyl, —OCH$_2$Ph, hydrogen, ethyl, t-butyl, —F, —SH, n-propyl, phenyl, —Cl, —SCH$_3$, i-propyl, methoxy, —Br, —SAc, ethoxy, —I, —SiH$_3$, n-butyl, —OPh, —OH, —NH$_2$, —COOH, —OAc, epoxy, —CF$_3$, —C(O)N(CH$^3$)$_2$, —CH=CH$_2$, —SO$_3$, —C(O)H, —NHC(O)Ph, —C≡CH, —C(O)NHCH$_3$, —NHCH$_2$Ph, —OPO$_3$, —OC(O)H, —P(O)(Cl)$_2$, —P(O)(OCH$_2$CH$_3$)$_2$, —P(O)(OCH$_3$)$_2$, —P(O)(OH)$_2$, —CH$_2$OH, —N=N—CH$_3$, —S(O)$_2$CH$_3$, —C(O)CH$_3$, —C=C=C(CH$_2$)$_2$, —CN, —P(CH$_3$)$_2$,

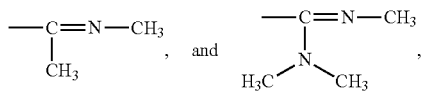

where Ph is phenyl and Ac is acetyl.

28. The use of any of paragraphs 26-27, wherein R$^4$ and R$^5$ are each independently selected from the group consisting of hydrogen, halogen, methyl, —OH, —COOH, —CN, —NH$_2$—N(CH$_3$)$_2$, —NO$_2$, —SH, and —SCH$_3$.

29. The use of any of paragraphs 26-28, wherein A is oxygen.

30. The use of any of paragraphs 26-29, wherein A is oxygen; R$^1$, R$^2$, and R$^3$ are each independently hydrogen or $C_1$-$C_6$ alkyl; R$^4$ and R$^5$ are each hydrogen; and n is 0.

31. The use of any of paragraphs 26-30, wherein R$^1$ is hydrogen, R$^2$ is methyl, and R$^3$ is methyl.

32. The use of any of paragraphs 26-31, where R$^1$ is methyl, R$^2$ is hydrogen, and R$^3$ is methyl.

33. The use of any of paragraphs 26-32, wherein the compound is a covalently linked with a carrier to form a prodrug.

34. The use of any of paragraphs 26-33, wherein the composition further comprises an effective amount of a therapeutic agent for treatment of diabetes.

35. The use of paragraph 34, wherein the therapeutic agent is selected from the group consisting of insulin, sulfonylurea, metformin, acarbose, repaglinide, nateglinide, pioglitazone, rosiglitazone, troglitazone, exenatide, dipeptidyl peptidase (DP) IV inhibitors, and combinations thereof.

36. The use of any of paragraphs 26-35, wherein the diabetes or related disorder is Type 1 diabetes, Type 2 diabetes, maturity-onset diabetes of the young (MODY), latent autoimmune diabetes adult (LADA), impaired glucose tolerance (IGT), impaired fasting glucose (IFG), gestational diabetes, and metabolic syndrome X.

37. The use of any of paragraphs 26-36, wherein the diabetes or related disorder is Type 2 diabetes.

38. The use of a compound according to any of paragraphs 1-7 to inhibit a FBPase by contacting the compound with the FBPase.

39. The use of paragraph 38, wherein said contact is in in vitro.

40. The use of any of paragraphs 38-39, wherein said contact is in in vivo.

41. The use of paragraph 39, wherein in vivo contact is in a mammal.

42. The use of any of paragraphs 39-41, wherein in vivo contact is in a human.

43. The use of any of paragraphs 39-42, wherein the in vivo contact is in a subject, where the subject suffers from diabetes or related disorders.

44. The use of paragraph 43, wherein the diabetes or related disorder is Type 1 diabetes, Type 2 diabetes, maturity-onset diabetes of the young (MODY), latent autoimmune diabetes adult (LADA), impaired glucose tolerance (IGT), impaired fasting glucose (IFG), gestational diabetes, and metabolic syndrome X.

45. The use of any of paragraphs 43-44, wherein the diabetes or related disorder is Type 2 diabetes.

The following examples demonstrate the preparation of compounds according to this invention. The examples are illustrative, and are not intended to limit, in any manner, the claimed invention.

EXAMPLES

A series of chemical compound related to achyrofuran, but involving less complex analogs, were synthesized.

Figures 2A, 2B:
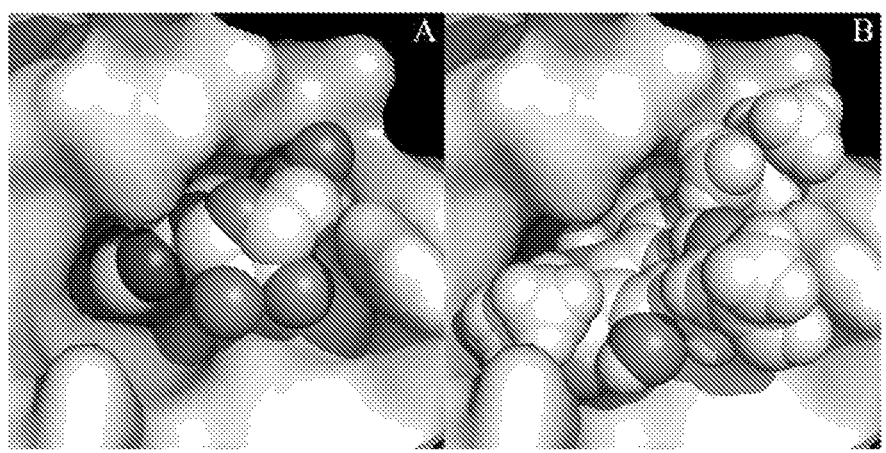
FIGS. 2A-2B show (A) AMP bound in the allosteric site of human FBPase. Drawing is based upon PDB code: 1FTA, chain A. (B) Achyrofuran (1) docked in the allosteric site of human FBPase using the XP mode of Glide (Schrödinger). This figure was created using PyMol[10].

Due to inventors' extensive work with inhibitors against FBPase, a visual inspection of 1 (achyrofuran) suggested that it might bind to the allosteric site of FBPase. See FIG. 1A. To test this hypothesis, the inventors docked each of the possible diastereomers of 1 using the high precision mode (XP) of Glide (Schrsdinger) into the allosteric site of human liver FBPase. Results showed that 1 binds with similar affinity to the allosteric site of FBPase as do AMP and MB05032. See FIG. 2.

In order to support the proposal that 1 was an inhibitor of FBPase, the inventors performed a substructure search to find a purchasable compound, as similar as possible to 1, that the inventors could test in vitro. From this search (+)-usnic acid (2), a naturally occurring dibenzofuran derivative found in several epiphytic lichen species, was identified. The XP mode of Glide was used to dock 2 into the allosteric site of FBPase. The results from Glide indicated that 2 had significant affinity for the allosteric site, although significantly less than 1. Activity measurements were performed to determine if 2 could act as an inhibitor of FBPase. As seen in Table 1, 2 inhibited both human liver and pig kidney FBPases with an IC$_{50}$ value of 0.37 and 0.93 mM, respectively.

Based upon the modeling of about twenty analogs, the inventors selected 3 and 4 (see examples 4 and 5, below) as their first targets because these compounds (I) docked with similar affinity to FBPase as achyrofuran, and (ii) could be readily synthesized using modifications of published procedures. As the stereochemistry at the three stereogenic centers on achyrofuran was not determined, 3 was particularly designed to possess no chiral centers while 4 was to be synthesized as a mixture of stereoisomers. The inventors also reasoned that in removing the methylpentenol and methylpentene groups, might also increase the hydrophilicity of the compounds.

The synthesis of compounds 3 and 4 is illustrated in Scheme 1. The synthesis of 6 was accomplished by the single iodination of commercially available 1,3,5-trimethoxybenzene (5) using solid iodine in the presence of iodic acid, as previously described with modifications.[11] As 1,3,5-trimethoxybenzene is a symmetrical molecule, the reaction was allowed to proceed freely without the need to control the position for substitution. Next, the biphenyl intermediate 7 was synthesized by Ullmann coupling.

Crafts acylation had successfully placed the isovaleryl functionalities on opposing sides of the ring. Having successfully synthesized 3, the inventors were able to apply the same strategy in synthesizing 4 by simply substituting isovaleryl chloride with 2-methylbutyryl chloride. Similar strategies as well as others known in the art can be used to synthesize compounds where $R_1$-$R_3$ (of Scheme 1) are combinations of, for example, methyl, ethyl, OMe, OEt, halogen, $NH_2$, SH, $SCH_3$, SAc, COOH, or CN functional groups.

Compounds 3 and 4 (see Scheme 1) were synthesized and tested to determine if they could inhibit either pig kidney or human liver FBPase. The test were performed using an enzyme-coupled assay[17] with AMP as a control. Compound 3 was found to inhibit pig kidney FBPase with an $IC_{50}$ of 1.5 µM as compared to 1.3 µM for the natural allosteric inhibitor, AMP, while the same compound inhibited human liver FBPase with an $IC_{50}$ of 8.1 µM as compared to 9.7 µM for

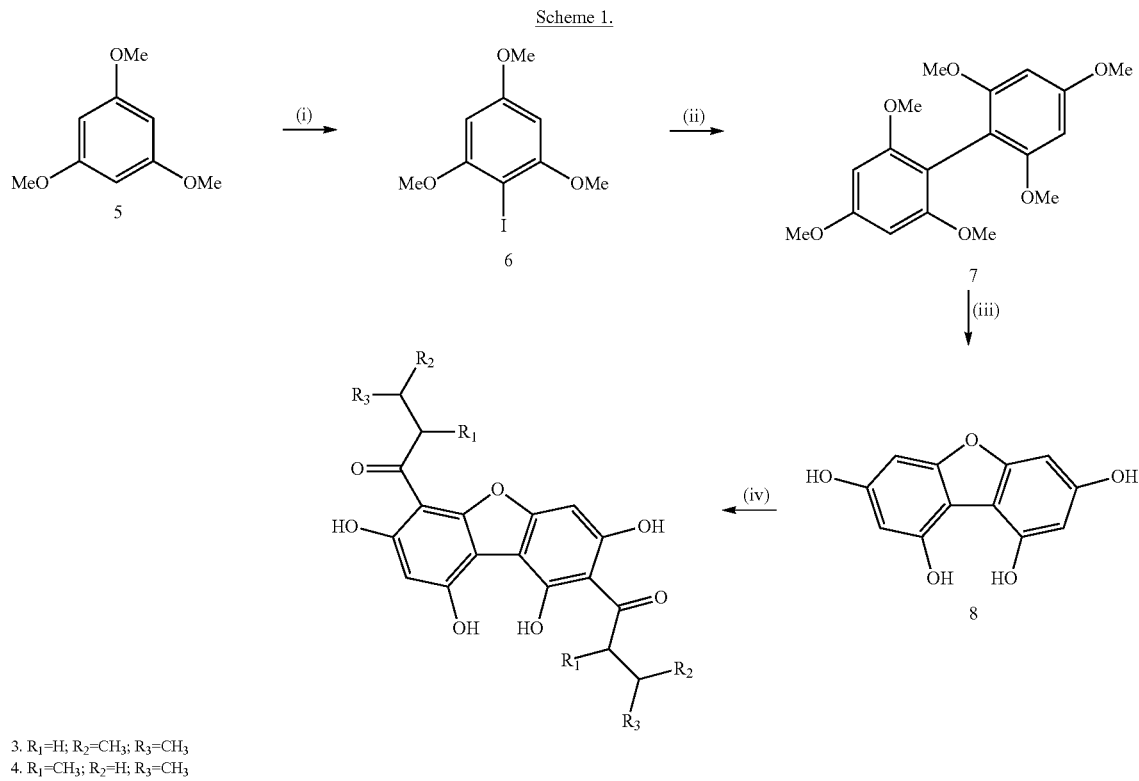

Conventionally, the Ullmann reaction is usually carried out in the presence of copper bronze,[11,12] but through the course of the synthesis, the inventors found that by substituting the copper bronze with solid copper, the inventors were able to obtain better yields. Cyclization and the concomitant deprotection of 7 in a 1:1 mixture of HBr and acetic acid,[13,14] conveniently yielded 8 as the key intermediate. Next, the inventors were faced with the challenge of functionalizing 8 with the appropriate acyl moiety. Attempts to introduce the isovaleryl group on the ring with isovaleryl chloride and tin (IV) chloride'[s] as well as with isovaleric acid and boron trifluoride[12] proved unsuccessful. The inventors reasoned that the isovaleryl portions could be strategically placed by means of the reaction with aluminum chloride[14,16] to ultimately yield 3. [1]H chemical shifts of the two dibenzofuran protons at 6.77 and 7.27, respectively, proved that the Friedel AMP. Compound 4, containing the 2-methylbutyryl functionality inhibited the pig and human FBPases with $IC_{50}$ values of 5.0 and 6.0 µM, respectively.

In order to confirm that the FBPase inhibition by the achyrofuran analogs was due to binding at the allosteric site and not the active site, a competition experiment was performed using the analog of AMP, 2',3'-O-(2,4,6-trinitrophenyl)adenosine 5-monophosphate (TNP-AMP). This analog has been shown to bind at the allosteric site of FBPase and exhibits fluorescence only bound when bound to the enzyme.[18] TNP-AMP was added to the FBPases at a concentration equal to 0.5 times their respective $K_d$. Increasing concentrations of 3 or 4 were added which resulted in a substantial diminution of the TNP-AMP fluorescence, indicating that both 3 and 4 were competing with TNP-AMP at the allosteric site. Binding constants for 3 and 4 could not be determined by this method due to the relatively low solubility of these compounds.

TABLE 1

Inactivation of human liver and pig kidney FBPase by intermediates and inhibitors.

| Compound | FBPase, IC$_{50}$ (μM) | |
|---|---|---|
| | Pig Kidney | Human Liver |
| AMP | 1.3 ± 0.1 | 9.8 ± 0.1 |
| Usnic Acid | 930 ± 11 | 371 ± 13 |
| 3 | 1.5 ± 0.1 | 8.1 ± 0.8 |
| 4 | 5.0 ± 0.3 | 6.0 ± 0.3 |
| 8 | ND* | ND |

*No detectable inhibition observed

The following experimental techniques were used:

Molecular Modeling

Docking of AMP and inhibitors to human liver and pig kidney FBPase was performed using Glide (Schrödinger, Inc.) in the high precision (XP) mode. The necessary grids were prepared based structures in the Protein Data Bank (PDB), namely 1FTA[20] and 1EYK[21] for the human and pig enzymes, respectively. The coordinates of AMP in the respective structures were used as the center of the grid box. 3D structures of AMP and inhibitors were generated using Maestro (Schrödinger, Inc.) and then processed through LigPrep (Schrödinger, Inc.), to produce a number of versions of the inhibitor structures with various ionization states, tautomers and stereochemistries as necessary for each case.

Isolation and Purification of Human Liver FBPase.

An expression plasmid (pEK694) for human liver FPBase was constructed by inserting the human liver FBPase gene from plasmid EX-C0133-B31 (GeneCopoeia) into the vector pET23a (Novagen, Inc.). The FBPase gene from EX-C0133-B31 had a C-terminal 6×His tag for use in purification.

For expression of the human liver FBPase, the plasmid pEK694 was transformed into BL21(DE3) Rosetta cells (Novagen, Inc.). A 5-ml overnight culture LB media22 with 150 μg/ml of ampicillin was back-diluted 1000-fold into 2 L of 2YT22 media with 0.4% glycerol and 150 μg/mL ampicillin. Bacterial growth at 37 C was monitored using the Abs560 and the doubling-time was calculated. When the growth reached an Abs560 of 0.4, cells were induced with 0.1 mM IPTG and allowed to grow for three additional doubling times. The cells were harvested by centrifugation (4400×g), resuspended in 5 mM K$_2$HPO$_4$, pH 7.4, 2.5 g/mL leupeptin, 0.1 mg/mL lysozyme and 50 mM imidazole and lysed by sonication. The lysate was clarified by centrifugation at 31,000×g for 15 min. The protein was purified through a Chelating Sepharose Fast Flow column (GE Healthcare) which had been charged with 0.3 M NiSO$_4$. Proteins that did not bind to the column were eluded with 10 column volumes of 50 mM imidazole, pH 7.5. The human liver FBPase was then eluted with buffer containing 50 mM sodium citrate and 50 mM NaCl, pH 4.0. The standard elution procedure using high concentrations of imidazole could not be used due to enzyme precipitation under these conditions. The protein-containing fractions were pooled together and dialyzed against 50 mM Tris-acetate buffer, pH 7.5 at 4° C. overnight. The precipitated protein was redissolved in 5 mM Na-malonate/Tris, 1 mM EDTA, 1 mM DTT, pH 5.5 and dialyzed extensively against 50 mM Tris, 150 mM NaCl, pH 7.5 at 4° C. for 24 h. Protein purity was confirmed by sodium dodecyl sulfate polyacrylamide gel electrophoresis.[23] Protein concentration was determined using the BioRadversionthe Bradford dye-binding as say[24] with bovine serum albumin as the standard.

Isolation and Purification of Pig Kidney FBPase

In order to more easily purify the pig kidney FBPase by metal chelating chromatography, six His residues were added to the C-terminal of the enzyme. This was accomplished by mutating the last two codons of the pig kidney FBPase sequence in plasmid pEK284[25] to a XhoI site, by site-specific mutagenesis. The new plasmid was then digested with XhoI and separated on an agarose gel. The larger fragment (4.6 Kb) was purified from the agarose gel and then religated by adding T4 DNA ligase at 12° C. for 12 hrs. The new plasmid pEK324 had the pig kidney coding sequence with the last two codons replaced with the codons for Leu-Glu-His-His-His-His-His-His.

Competent E. coli BL21(DE3) cells (Novagen, Inc.) were transformed with pEK324 and grown in YT[22] media at 37° C., containing 150 g/mL ampicillin. Bacterial growth at 37C was monitored using the Abs$_{560}$ and the doubling-time was calculated. When the growth reached an Abs$_{560}$ of 0.7, cells were induced with 0.4 mM IPTG and allowed to grow for an additional 18 h. The cells were harvested, purified according to the method described above for the human liver FBPase Measurement of FBPase Activity FBPase activity was measured spectrophotometrically by employing the coupling enzymes phosphoglucose isomerase and glucose-6-phosphate dehydrogenase.[17] The reduction of NADP+ to NADPH was monitored directly at 340 nm. Specifically, buffer (0.2 M Tris, 4 mM MgCl$_2$, 4 mM (NH$_4$)$_2$SO$_4$, 0.1 EDTA, pH 7.5), 0.2 mM of NADP+, 1.4 units of phosphoglucose isomerase and 0.5 units of glucose-6-phosphate dehydrogenase, 0-300M of inhibitor and 9 ng of FBPase, were mixed in a cuvette and equilibrated at 30° C. 70M of FBP was then added to initiate the reaction. Absdata were collected as a function of time using a JASCO V-630 spectrophotometer.

After a lag phase, due to coupling, a straight line was fitted to the progress curve and the slope value was recorded $_{asAbs340}$ per min. The amount of NADPH produced per minute was calculated using the 340 nm millimolar extinction coefficient of 6.22. At each inhibitor concentration, reactions were performed in duplicate. Inhibition curves were obtained for each compound by plotting the relative activity versus inhibitor concentration.

Fluorescence Measurements

Fluorescence data were collected using a JASCO FP-6300 spectro-fluorometer. Excitation and emission wavelengths of 410 and 535 nm respectively were used for TNPAMP (Molecular Probes). 0.15 mg of the respective FBPases, 0.08 mM MgCl and 20M fructose 1, 6-2 bisphosphate in 50 mM Tris-acetate buffer, pH 7.5, was added to a 2 mL cuvette and stirred. 3.5 M of TNP-AMP was added to the cuvette and the emission data was obtained Microliter volumes of 3 were subsequently added to the cuvette and resultant emission data was obtained after each addition. The final concentration of 3 in the enzyme solution was 6M. The competition experiment for 4 was performed in the same manner as described for 3.

Chemistry

All materials were reagent grade and used without further purification. Thin-layer chromatography (TLC) was performed on silica gel 60 aluminum backed pates (250 microns) from Sorbent Technologies and visualized by Abs$_{254}$ irradiation. Flash chromatography was conducted with silica gel 60 (230 mesh) from Ak Scientific Inc. $^1$H NMR spectra were recorded on a Varian 400 spectrometer. Proton chemical shifts are reported in ppm 0 relative to internal tetramethylsilane (TMS, 0.0) or with the solvent reference relative to TMS employed as the internal standard (CDCl$_3$, 7.24 ppm; DMSO-d$_6$, 2.50). Standard abbreviations indicating multiplicity were used as follows: s=singlet, d=doublet, t=triplet, q=quartet, m=multiplet and br=broad. Mass spectra were obtained at the Mass Spectrometry Facilities at Boston College. HPLC separations were performed on a Biologic Duo Flow chromatography system (Biorad).

Example 1

Synthesis of 2-Iodo-1,3,5-trimethoxybenzene (6)

1,3,5-Trimethoxybenzene (14.5 g, 0.086 mol) was dissolved in 10 mL of ethanol at rt before warming to 50° C. in a waterbath after which, an aqueous solution of iodic acid (7.6 g, 0.043 mol) was added. Solid iodine (21.88 g, 0.086 mol) was dissolved in 20 mL of ethanol and the resultant solution was added portion-wise over 60 min to the reaction mixture. Stirring was continued at 50° C. until the color of I faded and a white precipitate appeared. The reaction mixture$_2$ was stirred at room temperature for 18 h. The precipitate that formed was isolated via vacuum filtration, washed with ethanol and crystallized from methanol to yield 6 (21.7 g, 86%) as white crystals.

Example 2

Synthesis of 2,2',4,4',6,6'-Hexamethoxybiphenyl (7)

Compound 6 (7.0 g, 0.024 mol) and copper powder (2.0 g, 0.03 1 mol) were mixed thoroughly and transferred to a heavy wall, pressure vessel. The vessel was placed into a sand-bath at the initial temperature of 120° C. Once the vessel was secured, the temperature of the bath was raised to 235° C. in 15 min and kept at 235° C. for 1 h. The vessel was allowed to cool and the contents removed and powdered. The product was extracted with methanol for 18 h in a soxhlet. The resultant solution was concentrated in vacuo. Purification of the crude reaction mixture via column chromatography (1:5 ethyl acetate/hexane) yielded 7 (3.1 g, 78%) as a white solid.

Example 3

Synthesis of 1,3,7,9-Tetrahydroxydibenzofuran (8)

Compound 7 (3 g, 8.97 mmol) was refluxed for 18 h in a 20 mL solution consisting of a 1:1 mixture of HBr and acetic acid. The reaction mixture was neutralized by adding saturated aqueous NaHCO$_3$. The subsequent mixture was then extracted with ethyl acetate and the organic layer was further washed with brine, water and dried over Na$_2$SO$_4$. After removing the solvent in vacuo, the brown, viscous residue was purified by column chromatography (5-20% ethyl acetate/hexane) to yield 8 (1.6 g, 77%) as a yellow solid.

Example 4

Synthesis of 1,1'-(1,3,7,9-tetrahydroxydibenzofuran-2,6-diyl)bis(3-methylbutan-1-one) (3)

Compound 8 (100 mg, 0.431 mmol) and aluminum trichloride (287 mg, 2.15 mmol) were suspended in 5 mL of carbon disulfide at rt. Chloroform (6 mL) was added to the suspension and the reaction mixture was warmed to 50° C. in a water-bath. Isovaleryl chloride (259 mg, 2.15 mmol) was added dropwise and the reaction was stirred for 2 h at 50° C. After removing solvent in vacuo, and the crude reaction mixture was purified by column chromatography (1-5% ethyl acetate/hexane) to yield 3 (30 mg, 17%) as a white solid.

Example 5

Synthesis of 1,1'-(1,3,7,9-tetrahydroxydibenzofuran-2,6-diyl)bis(2-methylbutan-1-one) (4)

Compound 4 was synthesized according to the same procedure as described for 3, by substituting isovaleryl chloride with 2-methylbutyryl chloride (3.36 mmol, 429.0 L) to yield the desired product (40 mg, 15%) as white solid.

REFERENCES (1) Benkovic, S. J.; deMaine, M. M. Mechanism of Action of Fructose 1,6-bisphosphatase. *Adv. Enzymol.* 1982, 53, 45-82; Tejwani, G. A. Regulation of Fructose-bisphosphatase Activity. *Advan. Enzymol.* 1983, 54, 121-194; Van Schaftingen, E. Fructose 2,6-bisphosphate. *Adv. Enzymol. Relat. Areas Mol. Biol.* 1987, 59, 3 15-395.

(2) Van Schaftingen, E.; Hers, H. G. Inhibition of fructose-1, 6-bisphosphatase by fructose 2,6-biphosphate. *Proc Natl Acad Sci USA* 1981, 78, 2861-2863.

(3) Ke, H. M.; Liang, J. -Y.; Zhang, Y.; Lipscomb, W. N. Conformational transition of fructose-1,6-bisphosphatase: Structure comparison between the AMP complex (T form) and the fructose 6-Phosphate (R form). *Biochemistry* 1991, 30, 4412-4420; Ke, H. M.; Zhang, Y.; Lipscomb, W. N. Crystal structure of fructose 1,6-bisphosphatase complexed with fructose 6-phosphate, AMP and magnesium. *Proc. Natl. Acad. Sci. U.S.A.* 1990, 87, 5243-5247.

(4) Wright, S. W.; Carlo, A. A.; Carty, M. D.; Danley, D. E.; Hageman, D. L.; Karam, G. A.; Levy, C. B.; Mansour, M. N.; Mathiowetz, A. M.; McClure, L. D.; Nestor, N. B.; McPherson, R. K.; Pandit, J.; Pustilnik, L. R.; Schulte, G. K.; Soeller, W. C.; Treadway, J. L.; Wang, I. K.; Bauer, P. H. Anilinoquinazoline inhibitors of fructose 1,6-bisphosphatase bind at a novel allosteric site: synthesis, in vitro characterization, and X-ray crystallography. *J Med Chem* 2002, 45, 3865-3877.

(5) Erion, M. D.; van Poelje, P. D.; Dang, Q.; Kasibhatla, S. R.; Potter, S. C.; Reddy, M. R.; Reddy, K. R.; Jiang, T.; Lipscomb, W. N. MB06322 (CS-917): A potent and selective inhibitor of fructose 1,6-bisphosphatase for controlling gluconeogenesis in type 2 diabetes. Proc Natl Acad Sci USA 2005, 102, 7970-7975.

(6) von Geldern, T. W.; Lai, C.; Gum, R. J.; Daly, M.; Sun, C.; Fry, E. H.; Abad-Zapatero, C. Benzoxazole benzenesulfonamides are novel allosteric inhibitors of fructose-1, 6-bisphosphatase with a distinct binding mode. *Bioorg. Med. Chem. Lett.* 2006, 16, 1811-1815.

(7) Koehn, F. E.; Carter, G. T. The evolving role of natural products in drug discovery. Nat Rev Drug Discov 2005, 4, 206-220.

(8) Ajay, A.; Walters, W. P.; Murcko, M. A. Can we learn to distinguish between "drug-like" and "nondrug-like" molecules? J Med Chem 1998, 41, 3314-3324.

(9) Carney, J. R.; Krenisky, J. M.; Williamson, R. T.; Luo, J. Achyrofuran, a new antihyperglycemic dibenzofuran from the South American medicinal plant *Achyrocline satureioides.* J Nat Prod 2002, 65, 203-205.

(10) DeLano, W. L. The PyMol molecular graphics system, DeLano Scientific, Palo Alto, Calif., USA 2002

(11) Ahmad, S.; Razaq, S, New synthesis of biflavones of cupressuflavone series. Tetrahedron 1976, 32, 501-506.

(12) Carvalho, C. F.; Sargent, M. V. Naturally occurring dibenzofurans. Part 7. The synthesis of yrhodomyrtoxin. J. Chem. Soc., Perkin Trans. 1984, 11, 2573-2575.

(13) Sawada, T.; Aono, M.; Asakawa, S.; Ito, A.; Awano, K. Structure determination and total synthesis of a novel antibacterial substance, AB0022A, produced by a cellular slime mold. J. Antibiotics 2000, 53, 959-966.

(14) Giles, R. G. F.; Sargent, M. V. Naturally occurring dibenzofurans. X. A new synthesis of di-Omethylstrepsilin. Aust. J. Chem. 1986, 39, 2177-2181.

(15) Sargent, M. V.; Stransky, P. O, Naturally occurring dibenzofurans. Part 3. On the structures of the rhodomyrtoxins. J. Chem. Soc., Perkin Trans. 1983, 231-239.

(16) Hand, E. S.; Johnson, S. C.; Baker, D. C. Magnesium methyl carbonate-activated alkylation of methyl ketones with an w-halo nitrile, esters and amides. J. Org. Chem. 1997, 62, 1348-1355; Skene, W. G.; Berl, V.; Risler, H.; Khoury, R.; Lehn, J. M. Selective product amplification of thymine photodimer by recognition-directed supramolecular assistance. Org Biomol Chem 2006, 4, 3652-3663.

(17) Riou, J. -P.; Claus, T. H.; Flockhart, D. A.; Corbin, J. D.; Pilkis, S. J. In vivo and in vitro phosphorylation of rat liver fructose 1,6-bisphosphatase. Proc. Natl. Acad. Sci. U.S.A. 1977, 74, 4615-4619.

(18) Nelson, S. W.; Choe, J. Y.; Honzatko, R. B.; Fromm, H. J. Mutations in the hinge of a dynamic loop broadly influence functional properties of fructose-1,6-bisphosphatase. J Biol Chem 2000, 275, 29986-29992.

(19) Lipinski, C. A.; Lombardo, F.; Dominy, B. W.; Feeney, P. J. Experimental and computational approaches to estimate solubility and permeability in drug discovery and development settings. Adv Drug Deliv Rev 2001, 46, 3-26.

(20) Gidh-Jain, M.; Zhang, Y.; van Poelje, P. D.; Liang, J. Y.; Huang, S.; Kim, J.; Elliott, J. T.; Erion, M. D.; Pilkis, S. J.; Raafat el -Maghrabi, M.; et al. The allosteric site of human liver fructose-1,6-bisphosphatase. Analysis of six AMP site mutants based on the crystal structure. J. Biol. Chem. 1994, 269, 27732-27738.

(21) Choe, J. Y.; Fromm, H. J.; Honzatko, R. B. Crystal structures of fructose 1,6-bisphosphatase: mechanism of catalysis and allosteric inhibition revealed in product complexes. Biochemistry 2000, 39, 8565-8574.

(22) Miller, J. H. Experiments in Molecular Genetics. Cold Spring Harbor: Cold Spring Harbor Laboratory, 1972; Vol. NY.

(23) Laemmli, U. K. Cleavage of structural proteins during the assembly of the head of bacteriophage T4. Nature 1970, 227, 680-685.

(24) Bradford, M. M. A rapid and sensitive method for the quantitation of microgram quantities of protein utilizing the principle of protein-dye binding. Anal. Biochem. 1976, 72, 248-254.

(25) Lu, G.; Giroux, E. L.; Stec, B.; Kantrowitz, E. R. Evidence for an active T-state pig kidney fructose 1,6-bisphosphatase: Interface residue Lys-42 is important for allosteric inhibition and AMP cooperativity. Pro. Sci. 1996, 5, 2333-2342.

All patents and publications cited herein are hereby incorporated by reference.

What is claimed:

1. A compound according to formula (I)

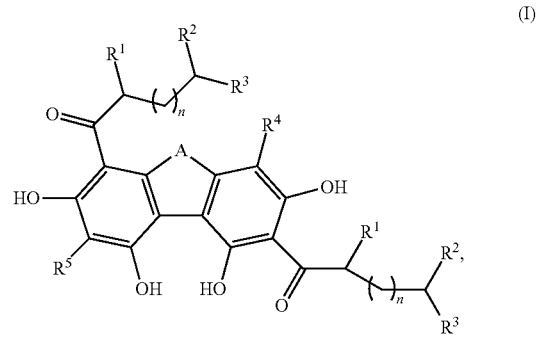

wherein,

A is oxygen, $CH_2$, sulfur, NH or, $NCH_3$;

$R^1$, $R^2$, and $R^3$ are each independently selected from the group consisting of hydrogen, halogen, branched or unbranched, substituted or unsubstituted $C_1$-$C_6$ alkyl, $C_2$-$C_6$ alkenyl, $C_2$-$C_6$ alkynyl, alkoxy, aryloxy, aryl, alkylaryl, alkoxyaryl, epoxide, —COOH, —CN, —$CX_3$, —$C(O)R^6$, —$C(O)N(R^6)_2$, —C═C═$C(R^6)_2$, —OH, —OAc, —$OC(O)R^6$, —$SO_3$, —$S(O)_2R^6$, —$S(R^6)$, —SAc, —NHC(O)Ar, —$NHCH_2Ar$, —$N(R^6)_2$, —N═$N(R^6)$, —$SiH_3$, —$P(O)(X)_2$, —$P(O)(OR^6)_2$, —$P(R^6)_2$, —$OPO_3$,

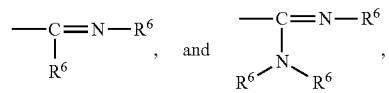

where X is a halogen, Ac is acetyl, and Ar is an aryl group; $R^4$ and $R^5$ are each independently selected from propyl, allyl and propargyl;

each $R^6$ is independently H or $C_1$-$C_4$ alkyl;

n is an integer from 0-5; and pharmaceutically acceptable salts, stereoisomer mixtures, and enantiomers thereof.

2. The compound of claim 1, wherein $R^1$, $R^2$, and $R^3$ are each independently selected from the group consisting of methyl, i-butyl, —$OCH_2Ph$, hydrogen, ethyl, t-butyl, —F, —SH, n-propyl, phenyl, —Cl, —$SCH_3$, i-propyl, methoxy, —Br, —SAc, ethoxy, —I, —$SiH_3$, n-butyl, —OPh, —OH, —$NH_2$, —COOH, —OAc, epoxy, —$CF_3$, —$C(O)N(CH^3)_2$, —CH═$CH_2$, —$SO_3$, —C(O)H, —NHC(O)Ph, —C≡CH, —$C(O)NHCH_3$, —$NHCH_2Ph$, —$OPO_3$, —OC(O)H, —P(O)$(Cl)_2$, —$P(O)(OCH_2CH_3)_2$, —$P(O)(OCH_3)_2$, —$P(O)(OH)_2$, —$CH_2OH$, —N═N—$CH_3$, —$S(O)_2CH_3$, —$C(O)CH_3$, —C═C═$C(CH_2)_2$, —CN, —$P(CH_3)_2$,

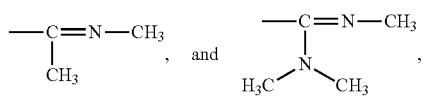

where Ph is phenyl and Ac is acetyl.

3. The compound of claim 1, wherein A is oxygen.

4. The compound of claim 1, wherein $R^1$ is hydrogen, $R^2$ is methyl, and $R^3$ is methyl.

5. The compound of claim 1, where $R^1$ is methyl, $R^2$ is hydrogen, and $R^3$ is methyl.

6. The compound of claim 1, wherein the compound is covalently linked with a carrier to form a prodrug.

7. A pharmaceutical composition comprising a pharmaceutically acceptable carrier and an effective amount of a compound according to claim 1 for treatment of diabetes.

8. A method for treating diabetes or related disorders, comprising administering to a subject in need thereof a pharmaceutical composition comprising a compound of claim 1, wherein the diabetes or related disorder is Type 1 diabetes, Type 2 diabetes, maturity-onset diabetes of the young (MODY), latent autoimmune diabetes adult (LADA), impaired glucose tolerance (IGT), impaired fasting glucose (IFG), gestational diabetes, and metabolic syndrome X.

9. The method of claim 8, wherein the administration step comprises administering 0.01 to 100 mg/kg of the compound.

10. The method of claim 8, wherein the administration step occurs within one hour before or after a meal.

11. The method of claim 8, wherein the composition further comprises an effective amount of a therapeutic agent for treatment of diabetes.

12. The method of claim 11, wherein the therapeutic agent is selected from the group consisting of insulin, sulfonylurea, metformin, acarbose, repaglinide, nateglinide, pioglitazone, rosiglitazone, troglitazone, exenatide, dipeptidyl peptidase (DP) IV inhibitors, and combinations thereof.

13. The method of claim 12, wherein the pharmaceutical composition further comprises a pharmaceutically acceptable carrier.

14. A method of inhibiting fructose-1,6-bisphosphatase (FBPase) comprising: contacting FBPase with a compound of claim 1 under conditions effective to inhibit said FBPase.

15. The method of claim 14, wherein said contact is in in vivo.

16. The method of claim 15, wherein the in vivo contact is in a subject, where the subject suffers from diabetes or related disorders, wherein the diabetes or related disorder is Type 1 diabetes, Type 2 diabetes, maturity-onset diabetes of the young (MODY), latent autoimmune diabetes adult (LADA), impaired glucose tolerance (IGT), impaired fasting glucose (IFG), gestational diabetes, and metabolic syndrome X.

* * * * *